United States Patent
Reineking et al.

(10) Patent No.: US 8,790,416 B2
(45) Date of Patent: Jul. 29, 2014

(54) NON-METAL TANNING PROCESS

(75) Inventors: Claus Reineking, Waldenbuch (DE);
Roberta Gamarino, Casale Monferrato (IT); Licia Trimarco, Saronno (IT); Maurizio Quaglierini, Chianni (IT); Markus Gisler, Rheinfelden (CH); Rainer Nusser, Neuenburg (DE)

(73) Assignee: Stahl International B.V., Waalwijk (NL)

( * ) Notice: Subject to any disclaimer, the term of this patent is extended or adjusted under 35 U.S.C. 154(b) by 0 days.

(21) Appl. No.: 13/879,207

(22) PCT Filed: Oct. 5, 2011

(86) PCT No.: PCT/EP2011/004974
§ 371 (c)(1),
(2), (4) Date: Apr. 12, 2013

(87) PCT Pub. No.: WO2012/055482
PCT Pub. Date: May 3, 2012

(65) Prior Publication Data
US 2013/0198974 A1    Aug. 8, 2013

(30) Foreign Application Priority Data
Oct. 28, 2010  (EP) .................................... 10014056

(51) Int. Cl.
*C14C 3/26* (2006.01)
*C14C 3/00* (2006.01)
*C14C 3/02* (2006.01)
*C14C 3/04* (2006.01)
*C14C 3/08* (2006.01)
*C07D 251/44* (2006.01)
*C07D 253/00* (2006.01)
*C07D 253/07* (2006.01)
*C07D 253/075* (2006.01)

(52) U.S. Cl.
CPC ... *C14C 3/00* (2013.01); *C14C 3/02* (2013.01); *C14C 3/04* (2013.01); *C14C 3/08* (2013.01); *C14C 3/26* (2013.01); *C07D 251/44* (2013.01); *C07D 253/00* (2013.01); *C07D 253/07* (2013.01); *C07D 253/075* (2013.01)
USPC ........................... 8/94.19 R; 8/94.21; 8/94.26

(58) Field of Classification Search
CPC .............. C14C 3/00; C14C 3/02; C14C 3/04; C14C 3/08; C14C 3/26; C07D 251/44; C07D 253/00; C07D 253/07; C07D 253/075
USPC ................ 8/94.19 R, 94.21, 94.26
See application file for complete search history.

(56) References Cited

U.S. PATENT DOCUMENTS

| 3,397,941 | A | 8/1968 | Heyden et al. |
| 5,501,708 | A * | 3/1996 | Pojer et al. ..................... 8/94.26 |
| 2013/0205516 | A1 | 8/2013 | Reineking et al. |
| 2013/0219634 | A1 | 8/2013 | Reineking et al. |
| 2013/0227798 | A1 | 9/2013 | Reineking et al. |
| 2013/0227799 | A1 | 9/2013 | Reineking et al. |
| 2013/0239340 | A1 | 9/2013 | Reineking et al. |
| 2013/0312200 | A1 | 11/2013 | Reineking et al. |

FOREIGN PATENT DOCUMENTS

| EP | 0950751 | 10/1999 |
| WO | WO 94/10345 | 5/1994 |
| WO | WO 02/50313 | 6/2002 |

OTHER PUBLICATIONS

STIC Search Report dated Nov. 25, 2013.*
PCT International Search Report for PCT/EP2011/004974, Jan. 4, 2012.
PCT International Preliminary Report on Patentability for PCT/EP2011/004974, Apr. 30, 2013.
Evans et al. "Colliagen Crosslinking: New Binding Sites for Mineral Tannage," J.A.L.C.A. vol. 82, pp. 88-95.
Bowes et al. "Crosslinking of Collagen," J. Appl. Chem 15 pp. 296-303, (Jul. 15, 1965).
English Abstract for EP 0950751, Oct. 20, 1999.

* cited by examiner

*Primary Examiner* — Eisa Elhilo
(74) *Attorney, Agent, or Firm* — Peacock Myers, P.C.; Jeffrey D. Myers

(57) ABSTRACT

Tanned leather, skin or pelt is produced by non-metal tanning, comprising the step of tanning a bated hide, skin or pelt with a tanning agent (A), the tanning agent (A) being at least one compound of a formula (I), $$\underset{X}{\overset{X}{\underset{\|}{\bigvee}}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\! \text{(I)}$$

wherein X signifies fluorine or chlorine, and/or $(^+NR_3)_{0-1}$, wherein R is a substituted or unsubstituted $C_1$ to $C_6$ alkyl group, a substituted or unsubstituted $C_6$ to $C_{10}$ aryl or a $C_5$ to $C_6$ heteroaryl group, R1 signifies hydrogen, $C_{1-8}$-alkyl or an alkyleneoxy radical of a formula (Ia), $-(-C_{2-3}$ alkylene-$O-)_q-H$ (Ia), R2 signifies hydrogen, hydroxyl, $C_{1-4}$-alkyl or $C_{1-4}$-alkoxy, m, signifies 1 or 2, n signifies 0 to 2, q is of from 1 to 10, M signifies hydrogen or an alkali metal cation or an ammonium cation, the ammonium cation being a protonated tertiary amine or a quaternary ammonium cation, in a tanning bath, the tanning bath having a pH of from 6 to 10 at the beginning of tanning step, wherein the bated hide or skin or pelt is subjected to tanning with (A) without previous pickling.

16 Claims, No Drawings

NON-METAL TANNING PROCESS

In the production of leather, the tanning process is of decisive importance for the properties and quality of the resulting leather. Among the various tannings known in the art, i.e. mineral, vegetable and synthetic, chrome-based tannage is a conventional and widely spread way of tanning which is readily feasible in an industrial scale on most various kinds of skins and hides, and provides tanned leathers with satisfactory properties (such as high shrinkage temperatures $T_s$, suppleness and suitability for subsequent processing such as neutralization, retanning, fat-liquoring, dyeing, finishing).

Chrome-based tanning agents and tannings are however considered environmentally unfriendly and it is therefore desired to provide other tanning methods.

In WO 02/50313 A2 it has been proposed to add certain laccase derived enzymes to the tanning bath with synthetic or vegetable tanning agents and then to add an oxidising agent. This adds however some further step in tanning and furthermore requires a particular precise control of the enzyme activity.

In WO 94/10345 A1 there is described a metal tanning in which in a first step (a) the substrate is pre-treated with certain compounds of the there defined formula (1) containing two substituents selected from carboxy and hydroxy, and a defined reactive group, and in a second step (b) a metal tannage is applied. Pre-treatment (a) is done in order to improve tanning with metal tanning agents in subsequent step (b).

In an article by Evans et al. in J.A.L.C.A. Vol. 82 (1987) pages 88-95, mentioned in the introduction of WO 94/10345 A1 and which relates to a pre-treatment of certain collagen substrates with 1,2-dicarboxylic acids and subsequent aluminium tannage, there is described the treatment of lambskin with 2-N-[bis-(3',4'-dicarboxyphenyl)methyl]methylamino-4,6-dichloro-s.triazine and subsequent tannage with basified aluminium sulphate. Also in this article the pre-treatment is done in order to improve tanning with the metal tanning agent (basified aluminium sulphate) in the subsequent tanning step.

J. H. Bowes and C. W. Cater in the article "Crosslinking of Collagen" in J. Appl. Chem., 15, Jul., 1965, describe some crosslinking tests carried out on collagen of denatured animal tendon (kangaroo tail tendon, KTT) with various crosslinking compounds—which need not act as complete tanning materials in themselves—in particular difluorodinitrodiphenylsulphone, diisocyanates, a number of aldehydes (formaldehyde, glyoxal, malonic dialdehyde, succinic dialdehyde, glutaraldehyde, adipic dialdehyde, acrolein and dialdehyde starch), cyanuric chloride and a number of cyanuric chloride derivatives (methoxy derivative, amino derivative hydrochloride, sulphonate derivative sodium salt, 5-sulphonaphth-1-ylamino derivative sodium salt, and bis-4,4'-diaminostilbene-2,2'-disulphonic acid derivative sodium salt)—in order to assess their crosslinking potentiality, and which could be combined with conventional tanning materials for improving resistance to deterioration due to moist heat and perspiration. From their measurements, finally, they conclude that aldehydes (glutaraldehyde) appear to be most promising because of number of crosslinks and stability, whereas cyanuric chloride derivatives would be less useful as crosslinking agents in collagen.

It has now surprisingly been found that a non-metal tanning of outstanding quality can be achieved using the below defined tanning agents—in particular even as complete tanning materials—and tanning methods, which also allow to omit a pickling as conventionally carried out before chrome tanning or aldehyde tanning, unless necessary for other reasons e.g. for degreasing. The invention relates to the tanning process, the defined tanning agent compositions, the use of the tanning agents and their compositions, the tanned leather, skin or pelt and its use for further processing.

As a non-metal tanning process there is meant herein a tanning produced without using any cationic metal compounds which have tanning activity, i.e. polybasic metal compounds, mainly chromium, aluminium, iron, zirconium or titanium salts etc. As a non-metal tanning agent there is meant herein a tanning agent that does not comprise any cationic metal compounds of tanning activity, i.e. polybasic metal compounds, mainly chromium, aluminium, iron, zirconium or titanium salts, etc.

In the following, alkyl means linear or branched alkyl, if not otherwise stated.

The invention thus firstly provides a process for the production of tanned leather, skins or pelts by non-metal tanning, comprising the step of tanning a bated hide, skin or pelt with a tanning agent (A), the tanning agent (A) being at least one compound of formula (I),

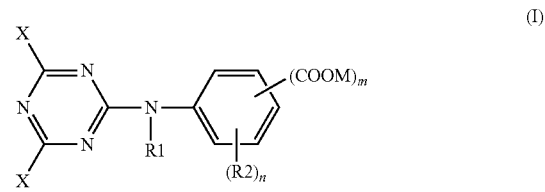

wherein

X signifies fluorine or chlorine, and/or $(^+NR_3)_{0-1}$, wherein R is a substituted $C_1$ to $C_6$ alkyl group or an unsubstituted $C_1$ to $C_6$ alkyl group, an unsubstituted $C_6$ to $C_{10}$ aryl group or a substituted $C_6$ to $C_{10}$ aryl group or a $C_5$ to $C_6$ heteroaryl group.

R1 signifies hydrogen, $C_{1-8}$-alkyl or an alkyleneoxy radical of formula (Ia),

$$-(-C_{2-3}\,\text{alkylene}-O-)_q-H \qquad (Ia)$$

R2 signifies hydrogen, hydroxy, $C_{1-4}$-alkyl or $C_{1-4}$-alkoxy,
m signifies 1 or 2,
n signifies 0 to 2,
q is of from 1 to 10,
M signifies hydrogen or an alkali metal cation or an ammonium cation, the ammonium cation being a protonated tertiary amine or a quaternary ammonium cation,
in a tanning bath, the tanning bath having a pH of from 6 to 10 at the beginning of tanning step, wherein the bated hide or skin or pelt is subjected to tanning with (A) without previous pickling.

The tanning agent (A) may consist of more than one compound of formula (I). In case of the tanning agent (A) containing a radical of formula (Ia) it may be a mixture of compounds of formula (I), in which q may also be calculated and expressed as an average number of alkyleneoxy units in the alkyleneoxy radical of formula (Ia) per compound of formula (I), based on all radicals of the formula (Ia) in the mixture. Preferably, the tanning agent (A) is only one compound of formula (I), in case that R1 is not the radical of the formula (Ia). In case, that R1 is the radical of the formula (Ia), the tanning agent (A) may also comprise compounds of formula (I) with a distribution of chain lengths of the radical of the formula (Ia).

X preferably signifies chlorine or fluorine. More preferably X signifies chlorine.

In case of q being of from 2 to 10, the alkylenoxy radical of formula (Ia) can also comprise a mixture of both ethylenoxy units and propylenoxy units.

If q is of from 2 to 10, then the radical of formula (Ia) preferably contains at least two ethyleneoxy units.

In case of compounds of formula (I) with q>5, preferably at least 40% of the total number of alkyleneoxy units in the radical of formula (Ia) are ethyleneoxy.

In case that the tanning agent (A) is a mixture of two or more compounds of formula (I) with R1 in these compounds of formula (I) being alkylenoxy radicals of formula (Ia), preferably the average q of alkylenoxy units per compound of formula (I) in the mixture is of from 1.0 to 10.0.

Any propylene in the alkyleneoxy radical of formula (Ia) is preferably a propylene-1,2.

R1 signifies preferably hydrogen or $C_{1-4}$-alkyl.

More preferably R1 is selected from the group consisting of hydrogen, methyl or ethyl.

R2 signifies preferably hydrogen, hydroxy-, methyl- or methoxy-group.

If m is 1, then the carboxy group is ortho-, meta- or para-position, with respect to the amino group —N(R1)— in formula (I). If m signifies 2, then the two carboxy groups are preferably in the positions 3 and 5, or 3 and 4.

n signifies preferably 0 to 1.

Where M is an alkali metal cation or a ammonium cation, then it may be any alkali metal cation or an ammonium cation as conventionally employed for salt formation in anionic compounds.

Preferably, the alkali metal cation is selected from the group consisting of lithium, sodium and potassium, more preferably the alkali metal cation is sodium. Preferably, the ammonium cation is a cation of formula (Ib),

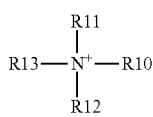

(Ib)

wherein

R10, R11, R12 and R13 are same or different and independently from each other selected from the group consisting of H, $C_{1-4}$-alkyl, $C_{2-3}$-hydroxyalkyl and benzyl, with the proviso, that only one of the four substituents R10, R11, R12 and R13 may be H.

Preferably,

R10 is H or $C_{1-4}$-alkyl, and

R11, R12 and R13 are same or different and independently from each other selected from the group consisting of $C_{1-4}$-alkyl, $C_{2-3}$-hydroxyalkyl; or R10, R11, R12 and R13 are same or different and independently from each other are $C_{1-4}$-alkyl; or R10, R11 and R12 are same or different and independently from each other are $C_{1-4}$-alkyl or $C_{2-3}$-hydroxyalkyl, and R13 is benzyl.

More preferably, the ammonium cation is selected from the group consisting of monohydrogen-tri($C_{2-3}$-alkanol)-ammonium, tetra($C_{1-4}$-alkyl)-ammonium, tri($C_{1-4}$-alkyl)-mono($C_{2-3}$-alkanol)-ammonium, di($C_{2-3}$-alkanol)-di($C_{1-4}$-alkyl)-ammonium, mono($C_{1-4}$-alkyl)-tri($C_{2-3}$-alkanol)-ammonium, monobenzyl-tri($C_{1-4}$-alkyl)-ammonium and monobenzyl-tri($C_{2-3}$-alkanol)-ammonium.

Especially, the ammonium cation is a quaternary ammonium cation.

More especially preferably, M is an alkali metal cation, even more especially preferably M is sodium.

Preferably, compound of formula (I) is a compound of formula (I-I),

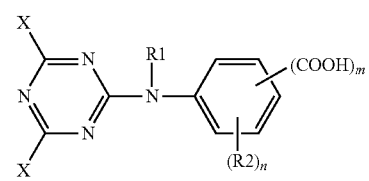

(I-I)

more preferably a compound of formula (I-II).

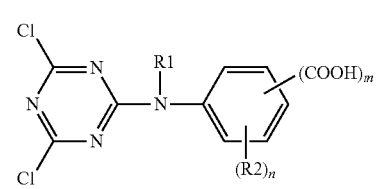

(I-II)

The compounds of formula (I) are known or may be produced according to known methods, preferably by reaction of a compound of formula (II),

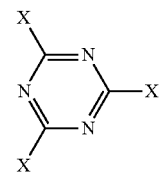

(II)

with a compound of formula (III),

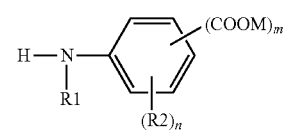

(III)

with X, R1, R2, m, n and M having the definition as given above, also with all their preferred embodiments.

The compounds of formula (III) are commercially available or may be produced according to known methods from known starting materials. Compounds of formula (III) with R1 not being H, may e.g. be produced by alkylation reaction of a compound of formula (IIIa)

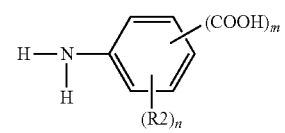

(IIIa)

by an alkylation reaction with an alkylating agent suitable for the introduction of the residue R1, e.g. a respective chloride or epoxide. If suitable the alkylation is done with intermediate protection of one of the two hydrogens connected to the nitrogen in formula (IIIa) by acetylation and subsequent hydrolysis after the alkylation reaction of the resulting acetylamino group.

The reaction of the compounds of formula (II) with the compounds of formula (III) is a reaction which splits off an acid H—X.

The reaction of the compound of formula (II) with the compound of formula (III) may be carried out in an aqueous, aqueous/organic or organic medium. Preferably, an aqueous solution or dispersion of compound of formula (III) is mixed with the compound of formula (II). The compound of formula (II) is preferably in form of a dry compound, an organic solution or dispersion or an aqueous dispersion. Preferably, an aqueous solution or dispersion of compound of formula (III) is added to an aqueous dispersion of compound of formula (II). In another preferred embodiment, the dry compound of formula (II) is stirred into a preferably aqueous solution or dispersion of compound of formula (III). The reaction is preferably carried out in the presence of a base or other reactant suitable for binding the acid H—X.

Suitable organic media include e.g. ethanol, isopropanol, acetone, methylethylketone, dimethylsulphoxide, chloroform, chlorobenzene and toluene. Preferably the reaction is carried out in aqueous medium.

Preferably, 1.00±0.05 mol of compound of formula (II) per mol of compound of formula (III) is used.

The concentration of compound of formula (II) is e.g. of from 2 to 70% by weight, preferably 5 to 50% by weight, the % by weight being based on the total weight of the reaction mixture comprising compound of formula (II), (III) and the aqueous, aqueous/organic or organic medium.

When the compound of formula (II) is dissolved in an organic medium, its concentration is preferably high, in particular close to saturation in order to reduce to a minimum the amount of solvent to be evaporated upon completion of the reaction.

Dispersion of compound of formula (II) or of compound of formula (III), preferably for dispersion in water, may be brought about by plain stirring or also by the use of a suitable surfactant (B) acting as a dispersing agent.

For dispersing a compound of formula (II) or a compound of formula (III), wherein the sulfonic acid group of compound of formula (III) is in protonated form, preferably for dispersing in water, surfactant (B) may be employed in a suitable efficient concentration, e.g. in a weight ratio of surfactant (B) to the compound of formula (II) or to the compound of formula (III) preferably of from 0.002 to 2, more preferably of from 0.004 and 1, even more preferably of from 0.005 and 0.5.

The compounds of formula (III) may be used in salt form, the salt form being preferably an alkali metal salt of the sulfonic acid, more preferably a sodium salt. The compounds of formula (III) in salt form are in general soluble in water and they are suitably employed in the form of an aqueous solution or dispersion (at concentrations higher than the one corresponding to the saturated solution), preferably in an amount of from 2 to 70% by weight, more preferably 10 to 50% by weight, the % weight being based on the total weight of the solution or dispersion of compound of formula (III). Preferably this solution or dispersion contains also a dispersing agent (B) as mentioned above, in a concentration as mentioned above suitable for dispersing compound of formula (II) when the latter is added as a dry product and is stirred into the solution.

According to a preferred embodiment, a compound of formula (II) is stirred into an aqueous solution of a compound of formula (III) containing a surfactant (B).

Where R1 is a radical of formula (Ia) with q being of from 2 to 10, the amount of surfactant (B) may be reduced or the use of surfactant (B) may even be omitted.

The surfactant (B) is preferably selected from the group consisting of (B1) non-ionic surfactant,
(B2) anionic surfactant,
(B3) cationic surfactant,
(B4) amphoteric surfactant and
mixtures of two or more thereof,
with the proviso that the surfactant (B) does not have a substituent capable of reacting with the compound of formula (II) under the chosen reaction conditions, in particular does not have a primary or secondary amino group. Preferable mixtures are mixtures of (B2) with (B1) and/or (B4), of (B3) with (B1) and/or (B4) or of (B1) with (B4).

Preferably, the non-ionic surfactant (B1) is selected from the group consisting of oligo- or polyglycolethers of aliphatic alcohols, oligo- or polyglycolesters of aliphatic carboxylic acids, oxyalkylated fatty acid amides and oxyalkylated partial esters of glycerol or sorbitol with fatty acids.

Preferably, the oxyalkylation of the fatty acid amides and the oxyalkylation of the partial esters of glycerol or sorbitol with fatty acids leads to oligo- or polyglycolether chains.

Preferably any oligo- or polyglycolether chain contains 2 to 60, more preferably 2 to 24 oxyalkylene units which are oxyethylene and optionally oxypropylene units, and preferably at least 40 mol-%, more preferably at least 50 mol-% being oxyethylene units and preferably, the non-ionic surfactant (B1) contains at least two oxyethylene units.

Preferably, the lipophilic aliphatic radical in the aliphatic alcohol, aliphatic carboxylic acids, fatty acid amides and fatty acids contain 8 to 24 carbon atoms.

The aliphatic radical may be saturated or unsaturated (preferably it contains only one double bond) and may be linear or branched, the branched preferably saturated.

As examples of aliphatic alcohols there may be mentioned lauryl, cetyl, myristyl, stearyl or oleyl alcohol, and $C_{9-15}$-oxoalcohols.

As examples of aliphatic carboxylic acids and of fatty acids amides there may be mentioned lauric, palmitic, myristic, stearic, behenic, arachic or oleic acid or amide.

The oligo- or polyglycolethers of aliphatic alcohols may be produced by oxyethylation and, if oxypropylene units are also to be present, oxypropylation of the corresponding aliphatic alcohols.

The oxyalkylated fatty acid amides may be produced e.g. by oxyethylation, and if oxypropylene units are also to be present, by oxypropylation of the corresponding fatty acid amides, e.g. of aliphatic acid diethanolamide or diisopropanolamide.

Oligo- or polyglycolesters and sorbitol monoesters may e.g. be produced by esterification of a corresponding oligo- or poly-ethylene- and optionally -propylene-glycolether or sorbitol. Monoglycerides may be partial saponification products of corresponding naturally occurring triglycerides.

Preferably, the anionic surfactant (B2) is selected from the group consisting of anionic polycarboxylates, aliphatic fatty acids in salt form (soaps), methyltaurides of aliphatic fatty acids and anionic derivatives of non-ionic surfactants, preferably of non-ionic surfactants (B1), in particular carboxymethylation products or carboxyethylation products of non-ionic surfactants (B1) or sulphuric acid monoesters or phosphoric acids monoesters of non-ionic surfactants (B1), in particular in alkali metal salt form.

Preferred anionic polycarboxylates are polyacrylates and polymethacrylates.

Preferably, the cationic surfactant (B3) is selected from the group consisting of tertiary or preferably quaternary derivatives of fatty amines, e.g. with 8 to 24 carbon atoms in the fatty amine chain, and in which the substituents of the tertiary amino group or quaternary ammonium group are $C_{1-4}$ alkyl (preferably methyl or ethyl) or hydroxyl-$C_{1-4}$-alkyl (preferably ethanol or isopropanol) and optionally benzyl, and where, if desired, the tertiary amino group or quaternary ammonium group may also contain an oligo- or polyglycolether chain analogously as mentioned above in the non-ionic surfactants (B1). As examples of fatty amines there may be mentioned lauryl, cetyl, myristyl, stearyl or oleyl amine and the amino group may be substituted with two methyl or ethyl groups and optionally a methyl or benzyl group, or with three methyl or ethyl groups or with two ethanol groups. If the tertiary amino group or quaternary ammonium group is oxyalkylated it may preferably contain a total of 2 to 40, more preferably 2 to 24 alkylenoxy groups, preferably at least 40 mol-% of which are ethyleneoxy and the remaining are propylenoxy. Tertiary amino groups are preferably protonated e.g. with hydrochloric, phosphoric or $C_{2-20}$-, preferably $C_{2-5}$-alkanoic acid.

Preferably, the amphoteric surfactants (B4) are anionic derivatives of (B3), e.g. carboxymethylation products of (B3), carboxyethylation products of (B3), sulphuric or sulphamic acid monoesters of (B3), or phosphoric acid mono- or diesters of (B3) of those cationic surfactants (B3) containing a hydroxy group, betaines and sulphobetaines.

Preferably, the surfactant (B) is a non-ionic surfactant (B1).

Preferably—in particular if in formula (I) R1 signifies hydrogen—non-ionic surfactants (B1) are used, more preferably the non-ionic surfactants (B1) are compounds of formula (IV) (polyglycolethers),

  (IV)

wherein
R3 signifies $C_{8-24}$-alkyl or $C_{8-24}$-alkenyl,
X is selected from the group consisting of —$CH_2$—$CH_2$—, —$CH_2$—$CH(CH_3)$—, —$CH(CH_3)$—$CH_2$— and combinations thereof, preferably of —$CH_2$—$CH_2$—, —$CH_2$—$CH(CH_3)$— and combinations thereof,
r signifies 2 to 60,
in case that the non-ionic surfactant (B1) of formula (IV) consists of more than one compound of formula (IV), r may also be calculated and expressed as the average number of radicals of the formula (IV) in the mixture,
with the proviso that the compound of formula (IV) contains at least two ethyleneoxy units, and with the proviso that at least 40% of the total number of alkyleneoxy units in the compound of formula (IV) are ethyleneoxy.

The reaction of the compound of formula (II) with the compound of formula (III) is preferably done at a temperature below 40° C., more preferably of from −10 to 40° C., even more preferably of from −10 to +25° C., especially preferably of from 0 to 15° C.

Preferably, the reaction of the compound of formula (II) with the compound of formula (III) is carried out under acidic to neutral pH conditions, more preferably at a pH of from 2 to 7, even more preferably under acidic conditions, especially preferably at a pH of from 2.5 to 6.

The base or other reactant which can be used for binding the acid H—X and which can be used for pH adjustment during the reaction of the compound of formula (II) with the compound of formula (III), is preferably selected from the group consisting of alkali metal base, quaternary ammonium hydroxide and carbonate.

The alkali metal base is preferably selected from the group consisting of hydroxide, carbonate and bicarbonate of lithium, sodium and potassium and mixtures thereof.

The quaternary ammonium hydroxide and carbonate is preferably selected from the group consisting of hydroxide and carbonate of tetramethyl-ammonium, tetraethyl-ammonium and benzyl-trimethyl-ammonium.

If an organic solvent has been used, this may be eliminated by evaporation and, if desired, the resulting product may be dissolved or dispersed in water. If a dry product is desired, this may be obtained from an aqueous solution or dispersion of the reaction product in a manner conventional per se, e.g. by precipitation (e.g. by salting out) and filtration, or by evaporation under controlled conditions.

A tanning agent (A) comprising more the one compound of formula (I) can be produced by using more than one compound of formula (III) in the reaction of compound of formula (II) with compound of formula (III), or by physical mixing the compounds of formula (I). The physical mixing can be done in dry form and/or in dissolved or dispersed form, preferably in dissolved or dispersed form in water.

The tanning agent (A) may be used as such, as produced, preferably in dry form or more preferably in the form of an aqueous solution or dispersion.

According to a particular aspect of the invention, the tanning agent (A) is in the form of an aqueous composition (T) which is free of any metal-based compounds which have tanning activity, aqueous composition (T) comprising the tanning agent (A) and water, and preferably comprises in addition the surfactant (B). Therefore, another subject of the invention is a tanning process as described above, also with all its preferred embodiments, wherein the tanning agent (A) is employed in the form of an aqueous composition (T) which is free of metal compounds of tanning activity.

More preferably, the composition (T) comprises of from 2 to 70% by weight, especially 10 to 50% by weight, the % by weight based on the total weight of the composition (T), of tanning agent (A).

Where surfactant (B) is present in the composition (T), the weight ratio of surfactant (B) to tanning agent (A) in the composition (T) is preferably of from 0.001 to 1, more preferably of from 0.002 to 0.4, even more preferably of from 0.005 to 0.1.

Preferably, in the composition (T), the surfactant (B) is the non-ionic surfactant (B1). If an anionic, cationic or amphoteric surfactant (B2), (B3) or (B4) is used, its amount is preferably of from 0.001 to 10 mol-%, the mol-% with respect to the total molar amount of tanning agent (A). More preferably the surfactant (B) is only the non-ionic surfactant (B1). If surfactant (B2) is a polycarboxylate, its amount is preferably <5% by weight, more preferably of from 0.01 to 4% by weight, even more preferably from 0.05 to 2% by weight, the % by weight being always based on the total weight of tanning agent (A).

The composition (T) has preferably an acidic to neutral pH, more preferably it has an acidic pH. For pH adjustment, a suitable buffer may be employed and composition (T) thus preferably further comprises a buffer (C1) to keep an acidic to neutral pH, preferably to keep an acidic pH, more preferably to keep a pH of from 1 to 7, even more preferably to keep a pH of from 1 to 5.

The buffer (C1) is preferably selected from the group consisting of phthalate, oxalate and citrate of sodium and/or of potassium, mono- and di-hydrogenphosphate of sodium and/ or of potassium, mixture of phosphoric acid and di-hydrogenphosphate of sodium and/or potassium and mixtures thereof, preferably a combination of $KH_2PO_4$ or $NaH_2PO_4$ and $Na_2HPO_4$ or $K_2HPO_4$.

The amount of buffer (C1) in the composition (T) is preferably chosen so as to achieve the desired pH mentioned above. The amount of buffer (C1) is preferably of from 0.1 to 5% by weight, the % by weight being based on the total weight of the composition (T).

Compositions (T) advantageously may further comprise an agent (D) to protect against the damaging action of microorganisms, preferably, agent (D) is a bacteriostatic additive and/or a microbicide, e.g. a fungicide.

As agent (D) there may be employed commercially available products, which may be employed in small concentrations, in particular according to the commercially recommended ones. The amount of of agent (D) in the composition (T) is preferably of from 0 to 10% by weight, more preferably of from 0.01 to 10% by weight, even more preferably of from 0.02 to 1% by weight, the % by weight being based on the total weight of the composition (T).

According to a particular further feature of the invention, aqueous compositions (T) may further comprise a polysaccharide-based thickener (E).

As thickener (E) there may be employed products known per se, in particular gums, carbohydrates, carbohydrate derivatives, e.g. pectins and hydrophilic cellulose derivatives, which with water form viscous solutions (colloidal or true solutions). There may be mentioned gums as obtainable by fermentation and optionally chemical modification of natural plant-exudates, e.g. xanthan gum, tragacanth gum, guar gum, carrageenan gum, alginate gum, agar gum, gum ghatti, and water soluble carbohydrate derivatives in particular pectins, e.g. pectins from fruits (e.g. citric fruits or apples) and amylopectins (e.g. from corn starch or potato starch), and hydroxyethylcellulose. The gums, carbohydrates and carbohydrate derivatives may also be chemically modified, provided that they do not contain any substituents capable of reacting with tanning agent (A) under storage or application conditions, in particular they do not contain any basic amino groups, especially any primary or secondary amino groups.

Thickener (E) may be employed in a minor proportion in the composition (T), in particular as suffices for adjusting the viscosity of (T) so that it is still flowable. Where thickener (E) is employed in the composition (T), it is added preferably in such a concentration that the viscosity of the composition (T) at 20° C. is preferably ≤10,000 mPa·s, more preferably of from 200 to 10,000 mPa·s, even more preferably of from 300 to 2,500 mPa·s, especially preferably 600 to 1,500 mPa·s. The viscosity is the Brookfield rotational viscosity, spindle no. 3, 20 rpm.

Preferably the amount of thickener (E) in the composition (T) is of from 0 to 5% by weight, more preferably of from 0.1 to 5% by weight, the % by weight based on the total weight of the composition (T).

Preferred compositions (T) are compositions (T1) comprising, in addition to the tanning agent (A), surfactant (B) and/or buffer (C1), more preferably surfactant (B) or surfactant (B) and buffer (C1); preferably compositions (T1) further comprise an agent (D) and/or a thickener (E).

Therefore, another preferred embodiment of the invention is a tanning process as described above, also with all its preferred embodiments, wherein the composition (T) is an aqueous composition (T1) comprising the tanning agent (A) and further comprising a surfactant (B) and/or a buffer ($C_1$) to keep an acidic to neutral pH.

Therefore, another preferred embodiment of the invention is a tanning process as described above, also with all its preferred embodiments, wherein the composition (T) is an aqueous composition (T1) of a tanning agent (A) comprising a surfactant (B) and/or a buffer ($C_1$) and further comprising an agent (D) to protect against the damaging action of microorganisms and/or a polysaccharide-based thickener (E).

Preferably, the composition (T) is a composition (T1) comprising of from 2 to 70% by weight, preferably 10-50% by weight, of tanning agent (A), the % by weight based on the total weight of the composition (T1);

surfactant (B) in a weight ratio of surfactant (B) to tanning agent (A) of from 0.001 to 1, more preferably of from 0.002 to 0.4, even more preferably of from 0.005 to 0.1;

buffer (C1) in such an amount as to achieve a pH in the composition (T1) of from 1 to 7, more preferably pH 1 to 5, preferably the amount of buffer (C1) is of from 0.1 to 5% by weight, the % by weight being based on the total weight of the composition (T1);

of from 0 to 10% by weight, preferably of from 0.01 to 10% by weight, more preferably of from 0.02 to 1% by weight, of agent (D), the % by weight based on the total weight of the composition (T1), thickener (E) in such an amount that the viscosity of the composition (T1) at 20° C. (Brookfield rotational viscosity measured with spindle no. 3, 20 rpm) is ≤10,000 mPa·s, preferably of from 200 to 10,000 mPa·s, more preferably of from 300 to 2,500 mPa·s, even more preferably 600 to 1,500 mPa·s, especially thickener (E) is used in an amount of from 0 to 5%, more preferably of from 0.1 to 5% by weight, the % by weight based on the total weight of the composition (T1);

and the dry substance content of the composition (T1) is preferably of from 4 to 75% by weight, more preferably in the range of 10 to 60% by weight, the % by weight based on the total weight of the composition (T1).

The dry substance content of (T) or (T1) may be assessed in a manner conventional per se, e.g. by calculation based on the employed reactants and components—mostly by simple addition of the amounts of the substances (expressed in dry form) added for the production of (T) or (T1) and substracting any water formed during the reaction-, or, which is the preferable way, by substracting the water content determined in a conventional way, e.g. by titration, e.g. Karl Fischer titration, from the total weight of (T) or (T1).

Particularly preferably, composition (T) or (T1) is a composition (T2) which contains the thickener (E), preferably in an amount of 0.1% by weight, more preferably of from 0.1 to 5% by weight of (E), the % by weight based on the total weight of the composition (T2). The viscosity of the composition (T2) at 20° C. (Brookfield rotational viscosity measured with spindle no. 3, 20 rpm) is preferably in the range of 300 to 2,500 mPa·s, more preferably 600 to 1,500 mPa·s.

This composition (T2) is of satisfactory stability and is suitable for storage and shipment and is directly usable. It is readily dilutable with water and may be directly metered into the tanning drum, if desired.

As a substrate for the treatment with tanning agent (A), in particular for tanning, there may be used any conventional animal hides, skins and pelts as are in general employed for tanning, e.g. hides from cow, calf or buffalo (e.g. also as split hides), skins from goat, sheep or pig, buckskins and pelts; but also other hides and skins e.g. from other mammals (foal, camel, lama, kangaroo, wallaroo, wallaby), reptiles (snakes, lizards), fishes (shark) or birds (ostrich), woolled skins and furskins, may be used in the process of the invention.

The bated substrates (animal hides, skins or pelts) may have been processed in the beamhouse before tanning, i.e. trimmed, soaked, limed, delimed and bated in conventional way. Before deliming the limed hides, skins or pelts are usually fleshed and, if required, split and optionally scudded, shaved etc. and, if required, defatted and/or dehaired.

Bated hides, skins and pelts to be used as substrates in the process of the invention may have been produced in conventional way, in the beamhouse, in particular by deliming the limed substrates and bating, using known agents for each of the mentioned processing steps.

Deliming may have been carried out in conventional way with known compounds such as acids, ammonium salts of low molecular aliphatic carboxylic acids, ammonium sulphate or sodium phosphate. Optionally the deliming composition may contain an enzyme e.g. as mentioned below, so that, if desired, bating and deliming may at least in part be combined.

For bating there may be employed known proteolytic bates, in particular in the form of bating compositions based on conventional proteolytic enzymes, mainly bacterial proteases, fungal proteases, and pancreas enzyme. Occasionally also other enzymes may be employed, such as lipases, amylases and also other hydrolases. Pancreas enzyme alone or in admixture with other enzymes (e.g. lipases, amylases and also other hydrolases) is preferred. Commercial forms of such enzymes may be formulated together with other components, especially with some mineral carriers, saccharides or polysaccharides and/or a hydrotrope. For the purpose of the invention substrates conventionally bated with bating compositions based on pancreas enzyme are well suitable.

The above bating compositions are in particular of an optimum activity in the weakly basic pH range, more particularly at a basic pH≤11, and consequently the pH of the bated substrate is preferably in the weakly basic range, in particular a pH in the range of 7.5 to 11, more preferably 7.5 to 10.

Where the substrate has been delimed with acids, also acidic bates may be used, e.g. pepsins e.g. in the form of a solution of 2% pepsin in water and at a pH in the range of 3-4.

The tanning process of the invention is based on a true tanning with the tanning agent (A) leading to leathers, skins and pelts with characteristic true tannage properties, such as a reduction or elimination of swellability, reduction of deformability and augmentation of firmness, diminution of shrinkage in volume, surface and thickness by drying, and increment of the porosity of the fibre texture, and further rising of shrinkage temperature and fastness of the collagen fibre to hot water, and of being non-rotting.

As a "step" in the tanning process according to the invention there is meant any tanning step in a tanning process in which the tanning agent (A) acts on the non-tanned or not fully tanned substrate, i.e. pre-tanning, main tanning, or full or complete tanning (including also a combined tanning). The tanning agent (A) can thus be employed for pre-tanning, for main tanning, or for full (i.e. complete) tanning or for both pre-tanning and main tanning, and for combined tannings. The use of the tanning agent (A) as a full tanning agent or as both a pre-tanning agent and a main tanning agent is however the most relevant aspect of the invention.

The tanning process of the invention—which may be a one stage tanning, i.e. a full tanning, or a two stage tanning, i.e. a pre-tanning followed by a main tanning, or a combined tanning—can be carried out directly after bating.

The tanning process with the tanning agent (A) of the invention may be carried out in an aqueous, aqueous/organic or organic medium; suitable organic media include e.g. ethanol, isopropanol, acetone, methylethylketone, dimethylsulphoxide, chloroform, chlorobenzene and toluene. Preferably it is carried out in an aqueous bath, e.g. at a bath length of 30 to 400% by weight of water, preferably 40 to 200%, most preferably 40 to 100%, the % by weight based on the weight of the fleshed or (if the hide has been split) the split substrate, and at temperatures preferably of from 10 to 50° C., more preferably of from 10 to 40° C., even more preferably of from 15 to 40° C. Preferably tanning is begun at a temperature of from 10 to 35° C., more preferably of from 15 to 30° C., and at the end the temperature is allowed to raise preferably by 5 to 20 degrees, more preferably by 8 to 15 degrees, to an end temperature of from 20 to 40° C., preferably of from 25 to 40° C.

For the tanning process of the invention the tanning agent (A) is added in the tanning bath in an efficient concentration, preferably of from 0.5 to 20% by weight, more preferably of from 1 to 10% by weight, the % by weight being based on the weight of the fleshed or split substrate. The tanning agent (A) may be added in dry form or preferably in the form of an aqueous composition, preferably as mentioned above as a composition (T).

With particular preference a surfactant, in particular as mentioned above a surfactant (B), preferably a non-ionic surfactant (B1), and/or a buffer (C2) for nearly neutral to basic pH values, in particular pH 6, may be added in the tanning bath, in a weight ratio as suitable in order to achieve the desired pH at the beginning of the tanning step.

Therefore, another preferred aspect of the invention is a tanning process as described above, also with all its preferred embodiments, wherein the tanning bath comprises a buffer (C2) to achieve a nearly neutral to basic pH at the beginning of the tanning step.

As buffers (C2) there may be employed known buffers, preferably selected from the group consisting of sodium and/or of potassium bicarbonate, sodium and/or of potassium carbonate, sodium and/or of potassium hydrogen phosphate, sodium borate and trishydroxymethylaminomethane. Preferably buffer (C2) is a combination of $KH_2PO_4$ or $NaH_2PO_4$ and $K_2HPO_4$ or $Na_2HPO_4$. For the tanning process of the invention it is of particular advantage to employ compositions (T) as described above, which preferably already contain a surfactant (B) and optionally also agent (D) and/or thickener (E). The buffer (C2) may be added directly into the tanning bath. Preferably the buffer (C2) is added in a two-stage tanning before the main tanning step in order to set the pH of the main tanning bath. Compositions (T), in particular compositions (T1), are readily efficient for tanning. The composition may contain some salt as resulting as a by-product from the synthesis of the compound of formula (I) from the reaction of compound of formula (II) with compound of formula (III).

The tanning process of the invention is started at a pH of from 6 to 10, preferably of from 6 to 9, more preferably of from 6.5 to 8.5, in particular as suitable for inducing the reaction of tanning agent (A) with the substrate.

During the tanning, the pH gradually decreases spontaneously by a few pH units, in particular by from 1 to 4 pH units, to a pH in the nearly neutral to weakly acidic pH range, in particular to a pH of from 7 to 3.5, preferably of from 6.5 to 3.5. The process may thus be carried out under self-regulating pH conditions. If desired, however, the tanning reaction may be influenced by the addition of a minor proportion of acid (e.g. a mineral acid, e.g. sulphuric or phosphoric acid, or a low molecular carboxylic acid e.g. with 1 to 4, preferably 1 or 2, carbon atoms, e.g. formic or acetic acid), or by the addition of a minor proportion of base (alkali), e.g. in order to accelerate or decelerate the reaction and/or to shift the pH slightly towards more neutral values.

In the process of the invention pickling is not necessary and is omitted. Therefore, subject of the invention is a tanning process as described above, also in all its preferred embodiments, wherein the bated hide or skin or pelt is subjected to tanning with a tanning agent (A) without previous pickling.

If the tanning process is started at nearly neutral conditions, in particular at a pH in the range of 6 to 7.5, the pH may initially also be kept in this range or increased, to give a pH in the range of 6 to 9, by addition of a base.

Since no pickling and depickling is carried out, pretanning or full tanning may be carried out directly on the bated substrate. The pH at the beginning of the tanning process is preferably nearly neutral to basic, in particular in the range of 6.5 to 10, preferably 6.8 to 9, and during the treatment gradually decreases spontaneously by a few pH units, in particular by 1 to 4 pH units, to a nearly neutral to weakly acidic pH range, in particular 7 to 4, preferably 6.5 to 4.5. The temperature is preferably in the range of 10 to 40° C., more preferably 15 to 35° C. More particularly tanning is preferably begun at 10 to 30° C. more preferably 15 to 25° C., and at the end the temperature is allowed to rise by 5 to 20 degrees, preferably by 8 to 15 degrees, to 20 to 40° C., preferably 25 to 40° C.

The tanning process of the invention is very simple and may be carried out in a relatively short time, in particular within about 5 to 24 hours, preferably 6 to 12 hours.

After tanning the exhausted tanning bath may be drained off and the tanned leather, skin or pelt may be rinsed or washed e.g. one to three times with water (e.g. 100 to 600% by weight of water, preferably 250 to 400% by weight of water, the % by weight being based on the weight of the fleshed or (if the hide has been split) the split substrate), to which if desired some conventional surfactants may be added, in order to favour slippage of the grain. If desired also a biocide e.g. as mentioned above for (D), may be added during the process, e.g. into the last washing bath, as a preserving agent for the resulting tanned hide or skin or pelt.

If desired a further non-mineral tanning agent (F), which is different from (A), of anionic or/and ethylenically unsaturated character or/and containing groups of basic character may be applied before, after or together with tanning agent (A) in pre-tanning, in main tanning or in full tanning, preferably for pre-tanning before a main tanning with (A), or in combination with (A) in a main or full tanning, or/and preferably for a complementary tanning after a main or full tanning with (A), or even for retanning.

(F) preferably is selected from the group consisting of
(F1) a vegetable tanning agent,
(F2) a syntan,
(F3) a synthetic, semisynthetic or natural resin or polymer,
(F4) a tanning natural oil or modified oil, and
mixtures thereof.

As vegetable tanning agents (F1) there may be employed known vegetable tanning agents, in particular pyrogallol- or pyrocatechin-based tannins, e.g. valonea, mimosa, teri, tara, oak, pinewood, sumach, quebracho and chestnut.

As syntans (F2) there may be employed known synthetic tanning agents, in particular syntans derived from sulphonated phenols and/or naphthols, and/or sulphones or polymers of sulphones and/or sulphonated phenols and/or sulphonated naphthols with formaldehyde or acetaldehyde and optionally urea, among which sulphone-based products are preferred.

As synthetic or semisynthetic or natural resins or polymers (F3) there may be employed e.g. known polyacrylates, polymethacrylates, copolymers of maleic anhydride and styrene, condensation products of formaldehyde with melamine or dicyandiamide, lignins and natural flours. Among the synthetic or semisynthetic or natural resins or polymers (F3), those of anionic character (e.g. polyacrylates, polymethacrylates, lignin sulphonates and copolymers of maleic anhydride and styrene) and which are free of basic amino groups are designated herein as (F3-I).

As natural or modified oils (F4) there may be employed known natural triglycerides, e.g. rape seed oil, fish oils or their oxidised derivatives, sulphated, sulphonated or oxysulphited fish oils, or their oxidised derivatives, or surrogates thereof.

Tanning with (A) may be carried out as a full tanning, or as a pre-tanning before a non-metal main tanning, which may be carried out with a vegetable tanning agent or with a synthetic tanning agent other than (A)—e.g. as mentioned above as (F)—or also with a tanning agent (A) according to the invention, or as a main tanning after a non-metal or even non-mineral pre-tanning (which may be vegetable or synthetic) e.g. carried out with (F) mentioned above. Where the tanning with (A) of the invention is carried out as a main tanning subsequently to a vegetable pre-tanning or to a synthetic pre-tanning with syntans, the pH may if required be adjusted to the desired value between 6 and 10, e.g. by addition of an alkali metal carbonate, bicarbonate or formate for the tanning method of the invention.

According to a particular feature of the invention, the tanning agent (A) may be used in combination with another non-mineral tanning agent (F), preferably (F-I), (F-I) being selected from the group consisting of (F1), (F2) and (F3-I), e.g. in a weight ratio of (A) to (F-I) being of from 0.05 to 20, more particularly from 2 to 10. The concentration of the combined tanning agents may be as desired for achieving a defined tanning, e.g. of from of 0.5 to 20% by weight, preferably 1 to 10% by weight, the % by weight based on the weight of the fleshed substrate.

According to a further particularly preferred feature of the invention, the substrates are first tanned in one or two stages with (A) and then are subjected to a complementary tanning with a non-mineral tanning agent (F), which preferably is (F-II), (F-II) being selected from the group consisting of (F1) or (F2) and (F3). As a complementary tanning there is intended here an additional tanning step carried out after main or full tanning with (A), and which substantially does not modify the characteristic kind of properties of the leather, skin or pelt tanned with (A), but may improve some of the typical tannage properties. Typically it is carried out with a smaller amount of the complementary tanning agent (F) compared with the amount of the employed main or full tanning agent (A), preferably 5 to 80% by weight, preferably 10 to 60% by weight of (F), the % by weight based on the weight of the employed amount of (A). This complementary tanning may advantageously be carried out sequentially to the tanning with (A) under temperature conditions as mentioned above, e.g. 10 to 40° C., at bath lengths preferably as used for tanning with (A), e.g. in the range of 40 to 200% by weight of water, the % by weight being based on the weight of the fleshed or (if the hide has been split) the split substrate, and under pH conditions as resulting from the tannage with (A), preferably after rinsing with water, usually this pH may range in the scope of 4 to 7.

Complementary tanning with (F), preferably with (F-II), may be carried out in the tannery directly after tanning, or even after having rinsed, dried and optionally mechanically treated the tanned leather, skin or pelt.

At the end of the tanning process, after draining off of the exhausted tanning or complementary tanning bath, the tanned leather, skin or pelt may—if desired—be treated with one or more conventional additives e.g. one or more surfactants, preferably as mentioned above as (B), mainly (B1) or (B3), for protecting the grain from damaging friction, or/and with a preserving agent, preferably as mentioned above as (D).

The tanned leather, skins or pelts produced according to the invention, as described above, may be further treated in conventional way, i.e. may be drained, dried and mechanically treated as usual for storage and/or shipment.

According to another preferred feature of the invention, the substrates are first tanned in one or two stages with (A), optionally subjected to complementary tanning with (F) or (F-II), and then are retanned with (F).

Retanning with (F) may be carried out after having rinsed, dried and optionally mechanically treated the tanned leather, skin or pelt e.g. in the dye-house.

The process of the invention may be carried out in a very economic an simple way, as a pickling and depickling may be omitted, and further the tanning itself may be carried out with a minimum quantity of water, and also a neutralisation—as otherwise conventionally carried out e.g. after metal tanning—is not necessary.

By the process of the invention there may be achieved metal-free tanned leathers, skins or pelts (in particular "wet white" metal-free leathers) of outstanding properties, in particular shrinkage temperatures, softness and consistency, e.g. firm grain texture, and with satisfactory fastnesses, especially where (A) or respectively (T) is employed for a main or full tanning. If no vegetable tanning agents at all are used or if only white to light yellowish vegetable tanning agents are also used, there may be achieved according to the invention "non-metal white tanned" leathers, skins and pelts, in particular non-metal "wet white" leathers, of high quality and very light own colour, i.e. nearly white. Where vegetable tanning agents of brownish to reddish colour are also used, the shade of the resulting tanned leathers, skins and pelts will be correspondingly slightly more brownish or reddish. Where (A) is employed for full tanning or for pre-tanning and main tanning and is followed by (F), in particular (F-II), for complementary tanning, further increased shrinkage temperatures $T_s$ may be achieved.

The tanned leathers, skins and pelts produced as described are suitable for further treatment in conventional way, mainly by retanning and/or fat liquoring and optionally dyeing and/or finishing. Fat liquoring may be carried out with known fat liquoring agents. Retanning is preferably carried out with (F). By retanning them with (F) and fat liquoring there may be produced upon drying high quality crust leathers. For dyeing there may be employed known leather dyes (e.g. as defined and in particular listed in the "Colour Index edited by Society of Dyers and Colourists and American Association of Textile Chemists and Colorists") and there may be obtained dyeings of satisfactory properties, mainly colour penetration, colour yield and fastnesses. With those leathers, skins or pelts which are of very light own colour, i.e. are nearly white, as mentioned above, there may also be achieved dyeings of delicate shades (pastel shades) of very pleasant shade.

Conventional leather finishing agents may also be employed for finishing if desired.

Therefore, another subject of the invention is the use of the tanned leather, skins or pelts produced according to the process as described above, also with all its preferred embodiments, for further processing by at least one further treatment selected from the group consisting of (a) retanning with a further non-mineral tanning agent (F), which is different from the tanning agent (A),
(b) fat-liquoring,
(c) dyeing, and
(d) finishing.

preferably a and b and optionally c and/or d.

In the following examples the indicated percentages are by weight; the viscosities are Brookfield rotational viscosities measured at 20 rpm with spindle nr. 3 at 20° C. unless otherwise indicated.

EXAMPLES

Example 1

500 parts of water and 500 parts of crushed ice and are charged into a reactor with stirring. At this temperature 185 parts g of cyanuric chloride are added and stirring is continued for 10 to 15 minutes. In parallel the pH of a mixture of 135 parts of 4-Aminonbenzenecarboxylic acid in 500 parts of water is adjusted to 5 with aqueous 30% by weight of sodium hydroxide solution. Then the slightly acidic solution is added to the cyanuric chloride dispersion within 60 minutes. At this point 230 parts of an aqueous 30% by weight of sodium hydroxide solution, the % by weight based on the weight of the solution, are added over the course of 1-2 hours keeping the temperature below 10° C. and the pH in the range of 6 to 7. Near the end of the addition of the sodium hydroxide solution the temperature is allowed to raise to 14° C. There is obtained a white-yellowish emulsion (Composition 1) containing the compound of formula (1).

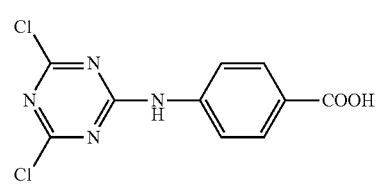

(1)

Example 2-20

The table which follows contains compounds of formula I-III which can be prepared similarly to the method described in Example 1 by using the corresponding starting materials.

(I-III)

| Example | X | R1 | R4 |
|---|---|---|---|
| 2 | Cl | Me | *–C₆H₄–COOH (para) |
| 3 | Cl | Et | " |
| 4 | Cl | H | *–C₆H₄–COOH (ortho) |
| 5 | Cl | Me | " |

-continued (I-III)

| Example | X | R1 | R4 |
|---|---|---|---|
| 6 | Cl | H | 3-COOH-phenyl |
| 7 | Cl | Me | " |
| 8 | Cl | H | 4-COOH-3-OH-phenyl |
| 9 | Cl | Me | " |
| 10 | Cl | H | 2-COOH-3-OH-phenyl |
| 11 | Cl | H | " |
| 12 | Cl | H | 4-CH3O-3-COOH-phenyl |
| 13 | Cl | Me | " |
| 14 | Cl | Et | " |
| 15 | Cl | H | 3,5-(COOH)2-phenyl |
| 16 | Cl | Me | " |
| 17 | Cl | H | 4-COOH-2-CH3-phenyl |
| 18 | Cl | Et | " |
| 19 | Cl | H | 2-COOH-4-CH3-phenyl |
| 20 | Cl | H | 3-COOH-4-COOH-phenyl |

Example 21

1,000 g of product obtained from example 1 and 400 ml of dimethylsulfoxide are charged into a reactor with stirring and 71 g of triethanolamine is added. The mixture is maintained under stirring at 40° C. for 12-15 hours. There is obtained a white-yellowish dispersion (Composition 21) containing the compound of formula (21)

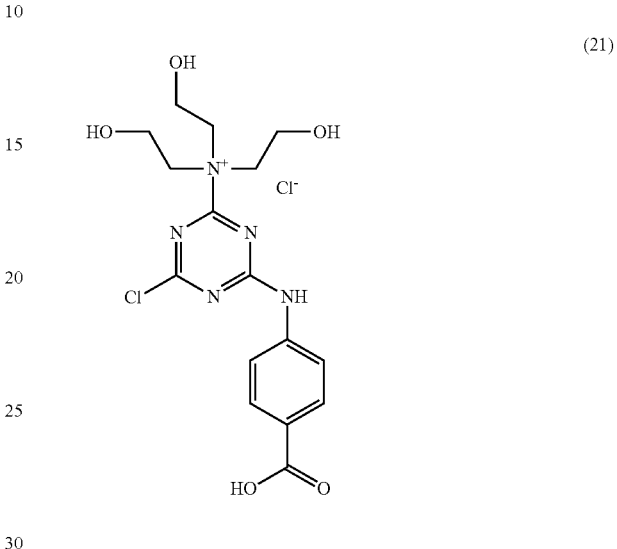

(21)

Example 22

1,000 g of the Composition 1 obtained according to Example 1 are pre-set at 20 to 25° C. and 10.2 g of disodium hydrogen phosphate, 8.7 g of monosodium dihydrogen phosphate and 2.0 g of NIPACIDE® BIT 20 (a commercial biocide based on 1,2-benzothiazolin-3-one of Nipa LAB's Ltd., from Nipa Laboratorien GmbH, Germany) are added with stirring. There is obtained a white-yellowish dispersion (Composition 22).

Example 23

100 g of water are heated to 50 to 55° C. At this temperature 4 g of hydroxyethylcellulose (having a viscosity of its 2% solution of 5,500 mPa·s at 25° C. and a pH of 7.0) are added and stirring is continued for 1 hour. There are obtained 104 g of hydroxyethylcellulose solution.

1,000 g of Composition 22 obtained in Example 22 are pre-set at 20 to 25° C. and 103.8 g of the hydroxyethylcellulose solution is added with stirring. There is obtained a white-yellowish suspension (Composition 23) having a viscosity of 1,250 mPa·s at 20° C.

Examples 24 to 61

Compositions of Examples 2 to 20 are converted like described with Composition 1 in Examples 22 and Composition 22 in Example 23 to yield Examples 24 to 61.

Example 62

1,000 g of the Composition 21 obtained according to Example 21 are pre-set at 20 to 25° C. and 10.2 g of disodium hydrogen phosphate, 8.7 g of monosodium dihydrogen phosphate and 2.0 g of NIPACIDE® BIT 20 (a commercial biocide based on 1,2-benzothiazolin-3-one of Nipa LAB's Ltd., from Nipa Laboratorien GmbH, Germany) are added with stirring. There is obtained a white-yellowish emulsion (Composition 62).

Example 63

100 g of water are heated to 50 to 55° C. At this temperature 4 g of hydroxyethylcellulose (having a viscosity of its 2% solution of 5,500 mPa·s at 25° C. and a pH of 7.0) are added and stirring is continued for 1 hour. There are obtained 104 g of hydroxyethylcellulose solution.

1,000 g of Composition 62 obtained in Example 62 are pre-set at 20 to 25° C. and 103.8 g of the hydroxyethylcellulose solution is added with stirring. There is obtained a white-yellowish suspension (Composition 63).

In the following Application Examples the indicated percentages—if not otherwise indicated—refer in Application Examples A to Ea) and Ia) to the weight of the split hide, in Application Examples Fa), Ga), Ha) and Hb) to the weight of the fleshed hide, in Application Examples Fb), Gb), and Ib) to the weight of the bated hide, in Application Example Hc) to the depickled weight of the substrate, in Application Example J to the weight of the depickled sheepskin and in Application Example K to the wet weight of the tanned leather. The shrinkage temperature $T_s$ is determined according to standard method IUP 16/ISO 3380-2006. Where a treatment is indicated to be carried out overnight, this is of 10 to 12 hours. If not otherwise indicated, pH is increased by addition of aqueous 10% by weight of sodium formate solution, the % by weight being based on the weight of the solution or is lowered by addition of aqueous 10% formic acid solution, the % by weight being based on the weight of the solution. The dyes are in commercial form blended with sodium chloride, with a dye content of around 60%, "C.I." stands for "Colour Index".

Application Example A a) Deliming and Bating:

Bovine limed hide (Swiss bull hide of the weight category 30 kg), fleshed and split to a thickness of 2.4 to 2.6 mm, is charged into a drum with 200% of water at 25° C., 0.1% of defatting agent ($C_{12-15}$ alkanol ethoxylated with 7 mols of ethylene oxide per mol of alkanol) and 0.2% of an ammonium based deliming agent (ammonium chloride and ammonium sulphate) and drummed for 20 minutes. Then the bath is drained, a fresh bath of 50% of water at 35° C., 0.1% of the above mentioned defatting agent and 0.5% of the above mentioned ammonium based deliming agent is charged into the drum and drumming is continued for 15 minutes. A further 0.5% of ammonium based deliming agent and 0.8% of a mixture of 70% boric acid and 30% mixed organic acids (adipic, glutaric and succinic acids in even parts) are added and drumming is carried on for 90 minutes. 0.6% of Feliderm® Bate PB1 p (a pancreas enzyme based bate of Clariant, Switzerland) is added and drumming is continued for 30 minutes and then the bath is drained. 300% of water is added and drumming is carried on for 15 minutes at 35° C. then the bath is drained.

b) Tanning:

A fresh bath of 50% water at 20° C. and 10% of Composition 22 according to Example 22 is added and drumming is carried on for 60 minutes, then the bath is heated during 120 minutes to 30° C. and drumming is continued overnight at 30-35° C. Then the bath is drained. 300% of water at 20° C. is added and drumming is continued for 30 minutes and then the bath is drained and the leather discharged and horsed up.

If desired 0.2% of Preventol® WB (a biocide of Bayer, Germany) is added to the last 300% of water.

The so obtained leather is then sammied and shaved to 2.0 to 2.2 mm.

Application Example B

The procedure described in Application Example A is repeated up to the tanning treatment with Composition 2 and drumming overnight at 30 to 35° C.

Complementary Tanning:

After drumming overnight 1% of a syntan based on sulphomethylated dihydroxydiphenylsulphone reacted with formaldehyde is added for complementary tanning and drumming is continued for 120 minutes and then the bath is drained. 300% of water at 20° C. is added and drumming is continued for 30 minutes and then the bath is drained and the leather discharged and horsed up. The so obtained leather is then sammied and shaved to 2.0 to 2.2 mm.

If desired 0.2% of Preventol® WB is added to the last 300% of water.

Application Example C

The procedure described in Application Example C is repeated up to the tanning treatment with Composition 3 and drumming overnight.

Complementary Tanning:

After drumming overnight 1% of syntan based on sulphomethylated dihydroxydiphenylsulphone reacted with formaldehyde is added for complementary tanning and drumming is continued for 120 minutes and then the bath is drained. 300% of water at 20° C. is added and drumming is continued for 30 minutes and then the bath is drained and the leather discharged and horsed up. The so obtained leather is then sammied and shaved to 2.0 to 2.2 mm.

Application Example D a) Deliming and Bating:

Bovine limed hide (Spanish bull hide of the weight category 30 kg), fleshed and not split is charged into a drum with 200% of water at 25° C., 0.1% of defatting agent ($C_{12-15}$ alkanol ethoxylated with 7 mols of ethylene oxide per mol of alkanol) and 0.2% of an ammonium based deliming agent (ammonium chloride and ammonium sulphate) and drummed for 20 minutes. Then the bath is drained, a fresh bath of 50% of water at 35° C., 0.1% of the above mentioned defatting agent and 0.5% of the above mentioned ammonium based deliming agent is charged into the drum and drumming is continued for 15 minutes. A further 0.5% of ammonium based deliming agent and 0.8% of a mixture of 70% boric acid and 30% mixed organic acids (adipic, glutaric and succinic acids in even parts) are added and drumming is carried on for 90 minutes. The pH is 7.8 and the cross section of the hide is colourless to phenolphthalein indicator solution. 0.6% of Feliderm® Bate PB1 p is added and drumming is continued for 30 minutes and then the bath is drained. 300% of water is added and drumming is carried on for 15 minutes at 35° C. then the bath is drained.

b) Tanning:

A fresh bath of 50% water at 20° C. is added. The pH is measured and adjusted to 8. 15% of Composition 23 according to Example 23 is added and drumming is carried on for 60 minutes, then the bath is heated to 30° C. and drumming is continued overnight at 30-35° C. Then the bath is drained off. 300% of water at 20° C. is added and drumming is continued for 20 minutes.

If desired 0.2% of Preventol® WB is added to the last 300% of water.

Then the bath is drained off, the leather is discharged and horsed up. The so obtained leather is then sammied and split and shaved to 1.4 to 1.6 mm.

Application Example E a) Deliming and Bating:

Bovine limed hide (Spanish bull hide of the weight category 30 kg), fleshed and not split is charged into a drum with 200% of water at 25° C., 0.1% of defatting agent ($C_{12-15}$ alkanol ethoxylated with 7 mols of ethylene oxide per mol of alkanol) and 0.2% of an ammonium based deliming agent (ammonium chloride and ammonium sulphate) and drummed for 20 minutes. Then the bath is drained, a fresh bath of 50% of water at 35° C., 0.1% of the above mentioned defatting agent and 0.5% of the above mentioned ammonium based deliming agent is charged into the drum and drumming is continued for 15 minutes. A further 0.5% of ammonium based deliming agent and 0.8% of a mixture of 70% boric acid and 30% mixed organic acids (adipic, glutaric and succinic acids in even parts) are added and drumming is carried on for 90 minutes. The pH is 7.8 and the cross section of the hide is colourless to phenolphthalein indicator solution. 0.6% of Feliderm® Bate PB1 p is added and drumming is continued for 30 minutes and then the bath is drained. 300% of water is added and drumming is carried on for 15 minutes at 35° C. then the bath is drained.

b) Pickling and Depickling:

70% of water at 20° C. and 7% of sodium chloride are added and drumming is carried on for 10 minutes. 0.8% of formic acid diluted 1:3 with water is added and drumming is continued for 30 minutes, then 1.5% of sulphuric acid diluted 1:10 with water is added and drumming is continued for 3 hours, then the pickle bath with the hide are allowed to dwell overnight with intermittent drumming of 5 minutes every hour. After this treatment the pH is 2.7 to 2.9. The bath is drained the hide is discharged and sammied. The drum is charged with 100% of water at 20° C. and 10% of sodium chloride, the drum is switched on and drumming is continued for 10 minutes, then the hide is charged into the drum and drumming is carried on for 30 minutes, then 1% of sodium bicarbonate is added and drumming is continued for 120 minutes, then the drum is stopped and the depickling bath with the hide are allowed to dwell overnight. The pH is about 8. Then the bath is drained off and the hide is rinsed with 200% of water at 20° C. for 15 minutes and then the bath is drained off.

c) Tanning

50% of water is added and the pH is adjusted to 8 by addition of 0.5% of sodium bicarbonate and 0.5% of sodium formate. The pH of the cross section of the hide is 8 (determined with phenolphthalein indicator). 15% of Composition 1 according to Example 1 is added and drumming is carried on for 1 hour, then the bath is heated to 35° C. and drumming is continued overnight at 35° C. Then the bath is drained off. 300% of water at 20° C. are added and drumming is continued for 20 minutes.

If desired 0.2% of Preventol® WB is added to the last 300% of water.

Then the bath is drained off, the leather is discharged and horsed up. The so obtained leather is then sammied and split and shaved to 1.4 to 1.6 mm.

Application Example F a) Deliming and Bating:

Bovine limed hide (Spanish bull hide of the weight category 30 kg), fleshed and split to a thickness of 2.4 to 2.5 mm, is charged into a drum with 200% of water at 25° C., 0.1% of defatting agent ($C_{12-15}$ alkanol ethoxylated with 7 mols of ethylene oxide per mol of alkanol) and 0.2% of an ammonium, based deliming agent (ammonium chloride and ammonium sulphate) and drummed for 20 minutes. Then the bath is drained, a fresh bath of 50% of water at 35° C., 0.1% of the above mentioned defatting agent and 0.5% of the above mentioned ammonium based deliming agent is charged into the drum and drumming is continued for 15 minutes. A further 0.5% of ammonium based deliming agent and 0.8% of a mixture of 70% boric acid and 30% mixed organic acids (adipic, glutaric and succinic acids in even parts) are added and drumming is carried on for 90 minutes. The pH is 7.8 and the cross section of the hide is colourless to phenolphthalein indicator solution. 0.6% of Feliderm® Bate PB1 p (a pancreas enzyme based bate of Clariant, Switzerland) is added and drumming is continued for 30 minutes and then the bath is drained. 300% of water is added and drumming is carried on for 15 minutes at 35° C. then the bath is drained.

b) Tanning:

A fresh bath of 50% water at 20° C. is added. The pH is 8. 10% of Composition 1 according to Example 1 is added and drumming is carried on for 60 minutes, then the bath is heated during 120 minutes to 30° C. and drumming is continued overnight at 30 to 35° C.

c) Complementary Tanning:

After drumming overnight 2% of Tara (commercial vegetable tanning agent, which is an aqueous composition of 50% by weight concentration, based on the weight of the composition, of an extract of the pods of *Caesalpinia Spinosa*) is added and drumming is continued for 3 hours at 35° C. Then the bath is drained off. 300% of water at 20° C. is added and drumming is continued for 30 minutes. Then the bath is drained off, the leather is discharged and horsed up. The so obtained leather is then sammied and shaved to 2.0 to 2.2 mm.

Application Example G a) Depickling:

Bated and pickled sheepskins are given into a drum with 100% of water at 20° C. and 10% of sodium chloride and drummed for 10 minutes. 1% of sodium bicarbonate and 1% of sodium carbonate are added and drumming is continued for 10 minutes then the bath is drained off. A fresh bath of 150% of water and 2% of defatting agent ($C_{12-15}$ alkanol ethoxylated with 7 mols of ethylene oxide per mol of alkanol) is added and drumming is continued for 1 hour, then the bath is drained off and a fresh bath of 150% of water and 2% of the defatting agent is added and drumming is continued for 1 further hour, then the bath is drained off. The skins are washed twice with each time 300% of water at 20° C., then the bath is drained off. The pH is 8.

b) Tanning:

50% of water at 20° C. and 20% of Composition 23 are added and drumming is continued for 2 hours then the temperature is raised slowly to 35° C., and drumming is continued at 35° C. overnight. The pH is 5.5. A fresh bath of 300% of water at 20° C. is added and after drumming for 30 minutes the bath is drained off, the leather is discharged, horsed up and sammied.

Application Example H

The leather obtained in Application Example D is retanned, fatliquored and dyed as follows:

The leather is charged into the drum, 200% of water at 25° C. and then 0.3% of defatting agent ($C_{12-15}$ alkanol ethoxylated with 7 mols of ethylene oxide per mol of alkanol) are added, the drum is switched on and drumming is carried on for 20 minutes. 0.5% acetic acid, diluted 1:10 is added and drumming is continued for 20 minutes. The pH is 4.5 and the cross section of the leather turns green by testing with Bromocresol Green indicator. The bath is drained off. 100% of water at 25° C. and then 1.6% of fatliquoring agent (oxysulphited fish oil) are added and drumming is continued for 20 minutes. 5% of a retanning syntan based on sulphomethylated dihydroxydiphenylsulphone reacted with formaldehyde and 5% of a phenolic syntan (reaction product of sulphonated phenol with formaldehyde and urea) are added and drumming is carried on for 2 hours. The bath is allowed to dwell overnight with intermittent drumming for 5 minutes every hour, then 0.5% of formic acid diluted 1:10 is added and drumming is carried on for 20 minutes, then the bath is drained off and the leather is washed with 200% of water. The bath is drained off. 100% of water at 50° C. is added followed by 5% of fat liquoring agents (3.5% alkylsulphosuccinate and 1.5% oxysulphited fish oil) and drumming is continued for 1 hour. After addition of 0.5% of formic acid drumming is carried on for 20 minutes and then the bath is drained off. The leather is rinsed for 5 minutes with 200% of water at 20° C. The bath is then drained off. 50% of water at 20° C. and 5% of the black dye C.I. Acid Black 210 is added and drumming is continued for 1 hour, then 200% of water at 50° C. and 1% of formic acid are added and drumming is continued for 10 minutes, then a further 1% of formic acid is added and drumming is carried on for 20 minutes, then the bath is drained off. 200% of water at 20° C. and 1.5% of a cationic surfactant 2-(8-heptadecenyl)-4,5-dihydro-1,3-bis(2-hydroxyethyl)-1H-imidazolium chloride are added and drumming is carried on for 15 minutes, then the bath is drained off and the leather is discharged. After 24 hours it is set out, vacuum dried at 60° C. during 2 minutes, dried hanging and staked. There is obtained a black dyed leather of satisfactory properties.

By employing 2% the brown dye C.I. Acid Brown 237 instead of the 5% of the black dye C.I. Acid Black 210, there is obtained a brown dyed leather of satisfactory properties.

Analogously as the leather from Application Example D also the leathers obtained according to each of Application Examples A to C, E to G are retanned, fat liquored and dyed according to the procedure described in Application Example H.

In the above Application Examples there are obtained leathers of satisfactory commercial grade in particular with satisfactory grain tightness, texture consistency (e.g. as resulting from some typical properties such as tensile strength, tear load and stitch tear resistance), softness, fastnesses and general appearance. In the dyeing examples there are further obtained dyed leathers of satisfactory properties in particular shade, dye penetration and colour yield, and fastnesses of the dyeing.

Application Example I a) Deliming and Bating:

Bovine limed hide (Spanish bull hide of the weight category 30 kg), fleshed and split to a thickness of 2.4 to 2.5 mm, is charged into a drum with 200% of water at 25° C., 0.1% of defatting agent ($C_{12-15}$ alkanol ethoxylated with 7 mols of ethylene oxide per mol of alkanol) and 0.2% of an ammonium based deliming agent (ammonium chloride and ammonium sulphate) and drummed for 20 minutes. Then the bath is drained, a fresh bath of 50% of water at 35° C., 0.1% of the above mentioned defatting agent and 0.5% of the above mentioned ammonium based deliming agent is charged into the drum and drumming is continued for 15 minutes. A further 0.5% of ammonium based deliming agent and 0.8% of a mixture of 70% boric acid and 30% mixed organic acids (adipic, glutaric and succinic acids in even parts) are added and drumming is carried on for 90 minutes. The pH is 7.8 and the cross section of the hide is colourless to phenolphthalein indicator solution. 0.8% of Feliderm® Bate PB1 p (a pancreas enzyme based bate of Clariant, Switzerland) is added and drumming is continued for 30 minutes and then the bath is drained. 300% of water is added and drumming is carried on for 15 minutes at 35° C. then the bath is drained.

b) Tanning:

A fresh bath of 50% water at 20° C. is added. The pH is 8. 20% of Composition 63 according to Example 63 is added and drumming is carried on for 60 minutes, then the bath is heated during 120 minutes to 30° C. and drumming is continued overnight at 30 to 35° C.

c) Complementary Tanning:

After drumming overnight 2% of Tara (commercial vegetable tanning agent, which is an aqueous composition of 50% by weight concentration, based on the weight of the composition, of an extract of the pods of *Caesalpinia Spinosa*) is added and drumming is continued for 3 hours at 35° C. Then the bath is drained off. 300% of water at 20° C. is added and drumming is continued for 30 minutes. Then the bath is drained off, the leather is discharged and horsed up. The so obtained leather is then sammied and shaved to 2.0 to 2.2 mm. If desired 0.2% of Preventol® WB is added to the last 300% of water.

The invention claimed is:

1. A process for the production of tanned leather, skin or pelt by non-metal tanning, comprising the step of tanning a bated hide, skin or pelt with a tanning agent (A), the tanning agent (A) being at least one compound of formula (I),

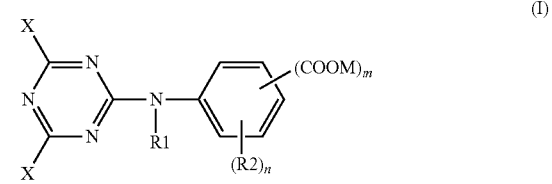

wherein
X is fluorine or chlorine ($^+NR_3)_{0-1}$ or a combination thereof, wherein R is a substituted $C_1$ to $C_6$ alkyl group, an unsubstituted $C_1$ to $C_6$ alkyl group, an unsubstituted $C_6$ to $C_{10}$ aryl group, a substituted $C_6$ to $C_{10}$ aryl group or a $C_5$ to $C_6$ heteroaryl group.
R1 is hydrogen, $C_{1-8}$-alkyl or an alkyleneoxy radical of formula (Ia), —($C_{2-3}$alkylene-O—)$_q$—H       (Ia)

R2 is hydrogen, hydroxy, $C_{1-4}$-alkyl or $C_{1-4}$-alkoxy, m is 1 or 2, n is 0 to 2, q is of from 1 to 10, M is hydrogen, an alkali metal cation or an ammonium cation, the ammonium cation being a protonated tertiary amine or a quaternary ammonium cation, in a tanning bath, the tanning bath having a pH of from 6 to 10 at the beginning of tanning step, wherein the bated hide or skin or pelt is subjected to tanning with (A) without previous pickling.

2. A process according to claim 1, wherein the tanning agent (A) is an aqueous composition (T) free of metal compounds of tanning activity.

3. A process according to claim 1, wherein the composition (T) is a composition (T1), the composition (T1) further comprising a surfactant (B) a buffer ($C_1$) or a mixture thereof to keep an acidic to neutral pH.

4. A process according to claim 3, wherein the composition (T1) further comprises an agent (D) to protect against the damaging action of microorganisms, a polysaccharide-based thickener (E) or a mixture thereof.

5. A process according to claim 1, wherein aqueous composition (T1) comprises a thickener (E).

6. A process according to claim 1, wherein the tanning bath comprises a buffer (C2) to achieve a nearly neutral to basic pH at the beginning of the tanning step.

7. A process according to claim 1, wherein the tanning step with the tanning agent (A) is a pre-tanning, a main tanning or a full tanning or a pretanning and a main tanning.

8. A process according to claim 7, wherein a non-mineral tanning agent (F), which is different from the tanning agent (A) is used before, after or together with tanning agent (A) in pre-tanning, in main tanning or in full tanning, or in combination with tanning agent (A) in full tanning.

9. A process according to claim 8, wherein the non-mineral tanning agent (F) is selected from the group consisting of (F1) a vegetable tanning agent, (F2) a syntan, (F3) a synthetic, semisynthetic or natural resin or polymer, (F4) a tanning natural oil or modified oil, and mixtures thereof.

10. A process according to claim 8, wherein the leather, skin or pelt is tanned with tanning agent (A) in a main or full tanning and then are subjected to a complementary tanning with the non-mineral tanning agent (F).

11. A process according to claim 8, wherein the non-mineral tanning agent (F) is employed in a smaller amount compared with the amount of the tanning agent (A).

12. A tanning agent (A) in a tanning process comprising at least one compound of formula (I),

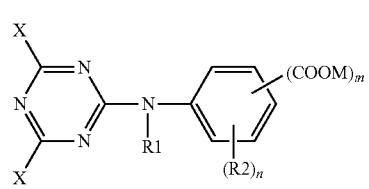

(I)

wherein

X is fluorine or chlorine ($^+NR_3$)$_{0-1}$ or a combination thereof, wherein R is a substituted $C_1$ to $C_6$ alkyl group, an unsubstituted $C_1$ to $C_6$ alkyl group, an unsubstituted $C_6$ to $C_{10}$ aryl group, a substituted $C_6$ to $C_{10}$ aryl group or a $C_5$ to $C_6$ heteroaryl group, R1 is hydrogen, $C_{1-8}$-alkyl or an alkyleneoxy radical of formula (Ia),

(Ia)

R2 is hydrogen, hydroxy, $C_{1-4}$-alkyl or $C_{1-4}$-alkoxy, m is 1 or 2, n is 0 to 2, q is of from 1 to 10, M is hydrogen, an alkali metal cation or an ammonium cation, the ammonium cation being a protonated tertiary amine or a quaternary ammonium cation.

13. A process according to claim 1, further comprising at least one further treatment selected from the group consisting of (a) retanning with a non-mineral tanning agent (F), which is different from the tanning agent (A), (b) fat-liquoring, (c) dyeing, and (d) finishing.

14. A process according to claim 1, further comprising a further treatment comprising retanning with a non-mineral tanning agent (F).

15. A process as according to claim 1, further comprising a further treatment comprising retanning with non-mineral tanning agent (F), fat-liquoring and optionally dyeing, finishing or a mixture thereof.

16. Tanned leather, skin or pelt made by the process according to claim 1.

* * * * *